US008139226B2

(12) United States Patent  (10) Patent No.: US 8,139,226 B2
Johnson  (45) Date of Patent: Mar. 20, 2012

(54) SOFT CLOCK DELAY FOR OCT SYSTEM AND METHOD THEREFOR

(75) Inventor: Bartley C. Johnson, North Andover, MA (US)

(73) Assignee: Axsun Technologies, Inc., Billerica, MA (US)

( * ) Notice: Subject to any disclaimer, the term of this patent is extended or adjusted under 35 U.S.C. 154(b) by 204 days.

(21) Appl. No.: 12/431,215

(22) Filed: Apr. 28, 2009

(65) Prior Publication Data
US 2010/0272432 A1  Oct. 28, 2010

(51) Int. Cl.
*G01B 9/02*  (2006.01)
(52) U.S. Cl. ........................................ 356/477
(58) Field of Classification Search .......... 356/477, 356/479, 484, 485, 497; 250/227.19, 227.27
See application file for complete search history.

(56) References Cited

U.S. PATENT DOCUMENTS

| 2007/0236700 A1* | 10/2007 | Yun et al. ........... 356/491 |
| 2008/0117430 A1* | 5/2008 | Terakawa et al. ........... 356/511 |
| 2008/0175465 A1* | 7/2008 | Jiang et al. ........... 382/131 |
| 2009/0046295 A1 | 2/2009 | Kemp et al. |
| 2009/0059971 A1* | 3/2009 | Atia et al. ........... 372/20 |
| 2009/0290167 A1* | 11/2009 | Flanders et al. ........... 356/497 |

OTHER PUBLICATIONS

Greengard, L., et al., "Accelerating the Nonuniform Fast Fourier Transform," SIAM Review, vol. 46, No. 3, pp. 443-454 (2004).
Sherif, S., et al, "Swept Source Optical Coherence Tomography with Nonuniform Frequency Domain Sampling," OSA/Biomed/DH/LACSEA, BMD86.pdf, 3 pages (2008).
Yun, S. H., et al., "High-Speed Spectral-Domain Optical Coherence Tomography at 1.3μm Wavelength," Opt. Express 11, 3598-3604 (2003).
U.S. Appl. No. 12/396,099, filed Mar. 2, 2009, entitled, "Optical Coherence Tomography Laser with Integrated Clock," by Dale C. Flanders et al.

\* cited by examiner

*Primary Examiner* — Michael A Lyons
(74) *Attorney, Agent, or Firm* — Houston Eliseeva, LLP

(57) ABSTRACT

An optical coherence analysis system comprises a swept source laser for generating optical signals that are tuned over a scan band; an interferometer for transmitting the optical signals over a sample arm and reference arm and combining the optical signals; a k-clock for generating a sampling clock indicating non-linearities in the frequency tuning of the optical signals over the scan band, the k-clock being not delay matched to propagation delays for the optical signals in the interferometer; a sampling system for sampling the optical signals from the interferometer in response to the k-clock to generate interference signals; and a processing system for determining non-linearities in the sampling clock and for transforming the interference signals into an image of a sample in response to the non-linearities. The system compensates for the lack of an electronic delay of k-clock using a nonuniform discrete Fourier transform.

22 Claims, 5 Drawing Sheets

SOFT CLOCK DELAY FOR OCT SYSTEM AND METHOD THEREFOR

BACKGROUND OF THE INVENTION

Optical Coherence Tomography (OCT) is a form of optical coherence analysis that is typically used to perform high-resolution cross sectional imaging. It is often applied to imaging biological tissue structures, for example, on microscopic scales in real time. Optical waves are sent through an object or sample and a computer produces images of cross sections of the object by using information on how the waves are changed.

A common type of optical coherence analysis is termed Fourier domain OCT (FD-OCT). These Fourier domain techniques often use a wavelength swept source and a single detector, sometimes referred to as time-encoded FD-OCT (TEFD-OCT) or swept source OCT (SS-OCT) since it has advantages in speed and signal-to-noise ratio (SNR). The spectral components are encoded in time. The spectrum is either filtered or generated in successive frequency steps and reconstructed before Fourier-transformation.

In TEFD-OCT, critical performance characteristics of the swept source laser are its tuning speed and accuracy. In order to compensate for instabilities and/or non-linearities in the tuning of the wavelength tuned laser, a sampling clock (k-clock) is employed to enable sampling at equally spaced increments in the optical frequency domain (k-space). This k-clock must usually be delayed to match the delay associated with the optical signals in the sample and reference arms of the interferometer of the OCT system.

If a k-clock is not used but the laser tunes non-linearly, other corrective options are employed. Some resample the data equally in k-space by interpolation, see S. Yun, G. Tearney, B. Bouma, B. Park, and J. de Boer, "High-speed spectral-domain optical coherence tomography at 1.3 µm wavelength," Opt. Express 11, 3598-3604 (2003), or employ a nonuniform discrete Fourier Transform (NDTF) that allows k to vary from an integral value, see S. Sharif, C. Flueraru, Y. M Mao, and S. Chang, Swept source Optical Coherence tomography with Nonuniform Frequency Domain Sampling," OSA/Biomed/DH/LACSEA, BMD86.pdf (2008).

Resampling in k-space has disadvantages. Typically, to accurately resample, oversampling must be employed, which adds overhead to the signal collection and processing. The Sharif-NDTF solution, since it does not involve a k-clock, relies on scan-to-scan stability in the swept source.

When a k-clock is used, transform-limited reconstruction of swept source OCT images at high speed requires that the frequency clock be well time-synchronized with the interference signal. FIG. 1 shows the computed point-spread function (FFT index) vs. clock delay. This plot shows the effect of clock and signal timing mismatch for a laser sweeping at 10 kHz. The required timing accuracy scales linearly with increases in sweep rate. The point spread function (PSF) is plotted as the clock delay is varied. This is a numerical experiment where real clock and interferometer signals were digitized with high time resolution. The PSF was reconstructed using this data with the clock mathematically advanced or retarded relative to the signal with a nominal delay of about 50 nanoseconds (ns) in the OCT interferometer. A delay 10 nanosecond causes a measureable difference the PSF; such delay corresponds to 2 meters of fiber. This effect would not exist if the laser could be swept linearly—that is at constant change in optical frequency per unit time. Practical limitations of the laser's tuning mechanism often prevent doing this to high accuracy. Generally, this problem becomes more severe with higher sweep frequencies.

The most common solution to delay matching the sampling clock to the interferometer delay is to use an optical delay. Simply, the optical signal used for the k-clock is transmitted through a length of optical fiber that has the same delay as the interferometer delay. The use of the optical delay leads to some logistical challenges such as managing the length of optical fiber used for the delay line, however.

In newer designs, the k-clock system is integrated with the swept laser source. An example is disclosed in U.S. patent application Ser. No. 12/396,099, filed on 02-MAR -2009, entitled Optical Coherence Tomography Laser with Integrated Clock, by Flanders, et al., U.S. Pat. Appl. Publ. No. US 2009/0290167 A1, which is incorporated herein by this reference. Here, the delay in the k-clock is provided electronically. This solution has certain advantages in that the electronic delay can be programmable to match changes in the interferometer delay that might be concomitant with the use of different OCT probes, for example.

SUMMARY OF THE INVENTION

While having advantages over optical delay solutions, the electronic clock delays can be costly in terms of the required electronics. One implementation uses a delay circuit based on emitter-coupled logic, or ECL. Such delay systems can be expensive and have relatively high power consumption since the transistors are operated in the saturation region, constantly drawing current.

The present invention concerns an alternate approach that is implemented in software. The electronic delay is eliminated at the cost of increased processing time and an additional calibration step during manufacturing. On the other hand, the overall system cost and size are reduced while yielding a system that is more flexible in its ability to compensate for different OCT probes, for example.

In general, according to one aspect, the invention features an optical coherence analysis system. The system comprises a swept source laser for generating optical signals that are tuned over a scan band, an interferometer for transmitting the optical signals over a sample arm and reference arm and combining the optical signals, a k-clock for generating a sampling clock indicating non-linearities in the frequency tuning of the optical signals over the scan band, the k-clock not being delay matched to propagation delays for the optical signals in the interferometer, a sampling system for sampling the optical signals from the interferometer in response to the k-clock to generate interference signals, and a processing system for determining non-linearities in the sampling clock and for transforming the interference signals into an image of a sample in response to the non-linearities.

In general, according to another aspect, the invention features an optical coherence analysis method. The method comprises generating optical signals that are tuned over a scan band, transmitting the optical signals over a sample arm and reference arm and combining the optical signals, generating a k-clock indicating non-linearities in the frequency tuning of the optical signals over the scan band that is not delay matched to propagation delays for the optical signals in the interferometer, sampling the optical signals from the interferometer in response to the k-clock to generate interference signals, and determining non-linearities in the k-clock and transforming the interference signals into an image of a sample in response to the non-linearities.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE PREFERRED EMBODIMENTS

Figure 1:
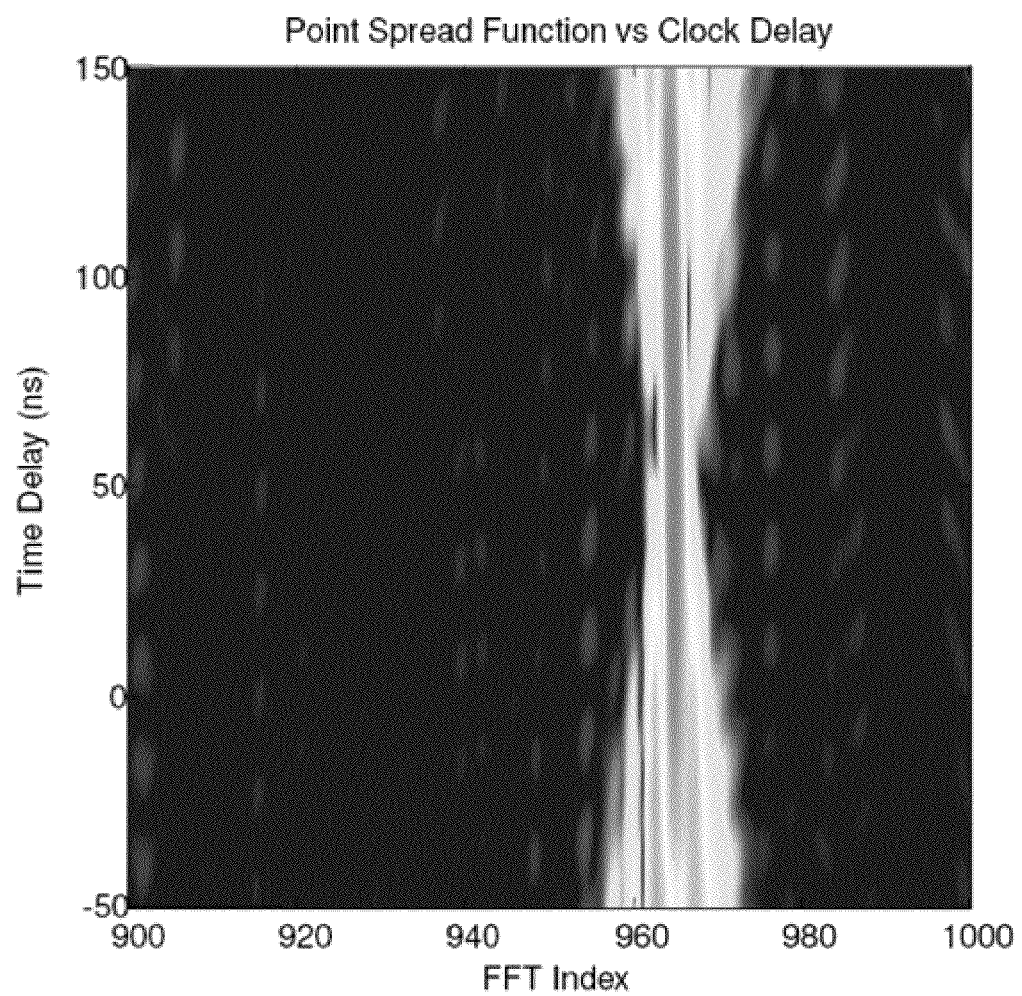
FIG. 1 is a plot of time delay in nanosecond (ns) as a function of fast Fourier transform index or PSF illustrating the change in the point spread function as a function of delay between the k-clock and sampling.
Figure 2:
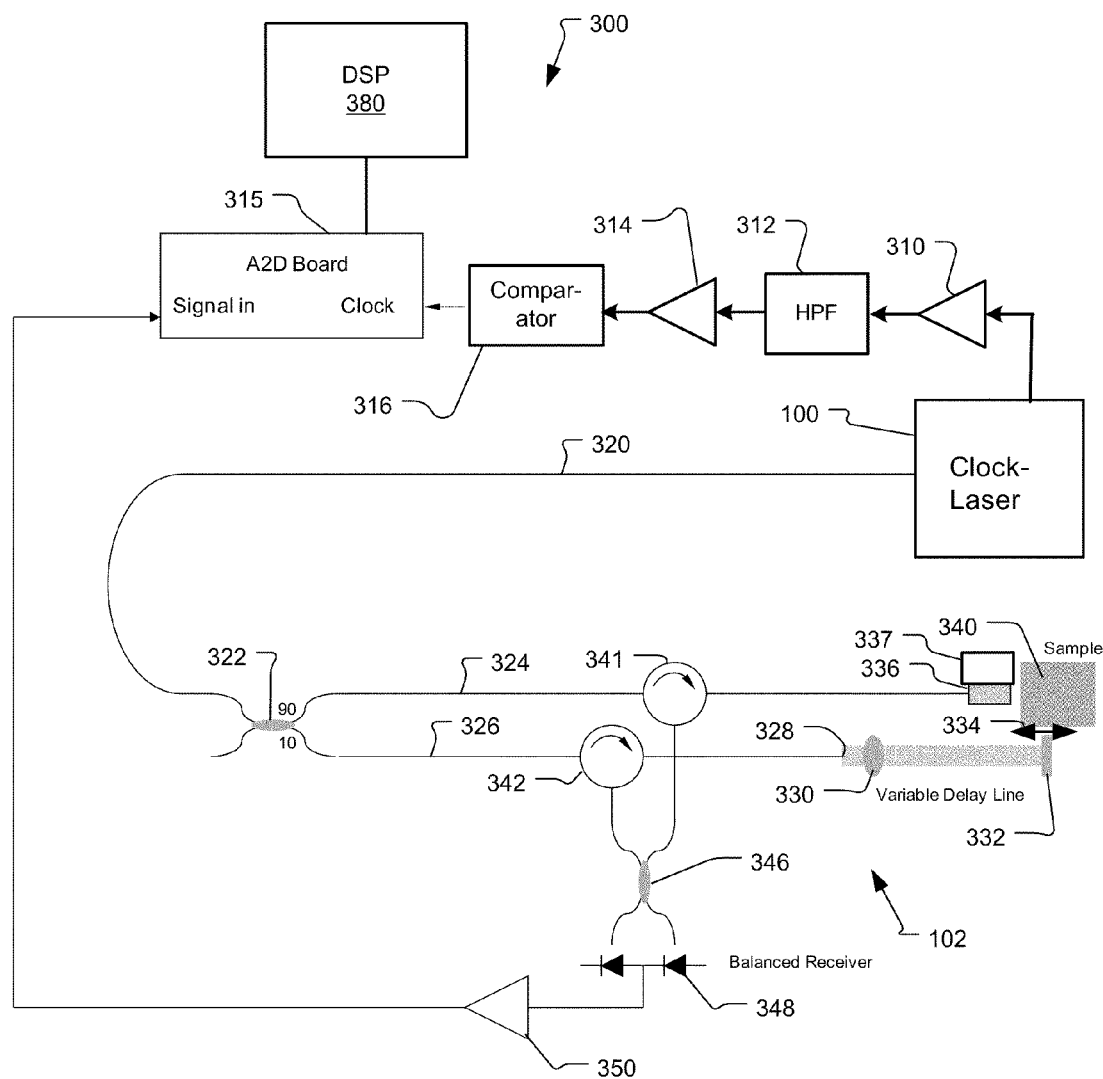
FIG. 2 is a schematic block diagram of an optical coherence analysis system according to the present invention.

FIG. 2 shows an optical coherence analysis system 300 using an integrated k-clock-swept source laser module 100 but without the typical delay for the k-clock. In the preferred embodiment, the k-clock-swept/source laser module 100 is constructed as described in incorporated U.S. patent application Ser. No. 12/396,099.

In more detail, a Michelson interferometer 102 is used to analyze the optical signals from the sample 340. Light from the swept source laser module 100 is output on fiber 320 to a 90/10 optical coupler 322. The tunable signal is divided by the coupler 322 between a reference arm 326 and a sample arm 324 of the system.

The optical fiber of the reference arm 326 terminates at the fiber endface 328. The light exiting from the reference arm fiber endface 328 is collimated by a lens 330 and then reflected by a mirror 332 to return back.

The external mirror 332 has an adjustable fiber to mirror distance (see arrow 334). This distance determines the depth range being imaged, i.e. the position in the sample 340 of the zero path length difference between the reference arm 326 and the sample arm 324. The distance is adjusted for different sampling probes and/or imaged samples. Light returning from the reference mirror 332 is returned to a reference arm circulator 342 and directed to a 50/50 fiber coupler 346.

The fiber on the sample arm 324 terminates at the sample arm probe 336. The exiting light is focused by the probe 336 onto the sample 340. Light returning from the sample 340 is returned to a sample arm circulator 341 and directed to the 50/50 fiber coupler 346. The reference arm signal and the sample arm signal are combined in the fiber coupler 346. The combined/interference signal is detected by a balanced receiver, comprising two detectors 348, at each of the outputs of the fiber coupler 346. The electronic interference signal from the balanced receiver 348 is amplified by amplifier 350.

In examples, the scanning is implemented by moving the probe 336 relative to the sample 340 using a two (x-y) dimensional or three (x-y-z) dimensional positioner 337. In other examples, the x-y-z scanning is implemented by moving the sample 340 relative to the probe 336. In still other examples, cylindrical scanning is implemented by rotating and axially moving the probe 336.

A k-clock signal is produced by the swept source laser module 100. As the optical signal from the swept source scans through the spectral scan band, the electronic k-clock signal from the clock laser 100 indicates each time the laser has scanned through another frequency increment. The k-clock signal from the clock laser 100 is further formed and conditioned by the transimpedance amplifier 310, high-pass filter 312, amplifier 314, and optional fast comparator 316.

It is important to note that the k-clock signal is not delayed and/or delay-matched, either electronically or with an optical delay, to the delay associated with the optical signal's propagation through the optical fibers in the arms of the interferometer 102.

An analog to digital converter system 315 is used to sample the interference signal output from the amplifier 350. The clock input of the k-clock provides time of the sampling at equally spaced swept optical frequency increments of scanning of the swept source tunable signal. It is important to note, that since the k-clock signal received by the A/D converter system 315 is not delay matched, the sampling of the interference signal does not in fact occur at equally spaced frequency increments when the scanning of the swept source of the laser clock module 100 is not linear due to changes in the frequency swept rate associated with the delay mismatch between the earlier-arriving k-clock signal relative to the later arriving interference signal. This total delay is a combination of the optical and electronic delay difference between the k-clock path and the interference signal path to the A/D converter system 315.

Once a complete data set has been collected from the sample 340 by the operation of the scanner 337 and the spectral response at each one of these points is generated from the tuning of the laser-laser clock module 100, the digital signal processor 380 performs a Fourier transform on the data in order to reconstruct the image and perform a 2D or 3D tomographic reconstruction of the sample 340. This information generated by the digital signal processor 380 is then displayed on a video monitor.

In the illustrated example, the k-clock is non delay matched to the signals from the interferometer, and further the tuning of the clock-laser is non-linear. So to compensate for this, the digital signal processor 380 transforms the interference signals into an image of a sample in response to the non-linearities so as to compensate for them. In the current embodiment, the digital signal processor 380 performs a nonuniform discrete Fourier transform on the interference signals using non-integer k-values determined in response to the non-linearities that are determined during a calibration process.

Figure 3:
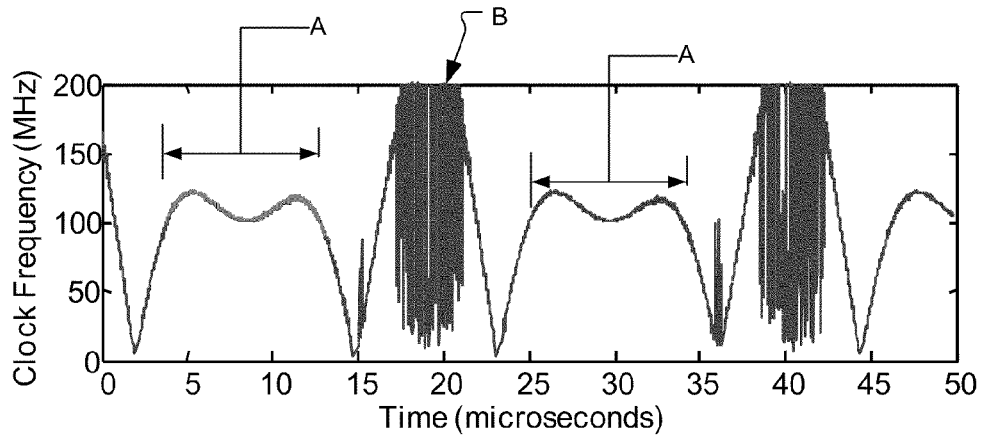
FIG. 3 is a plot of clock frequency as a function of time through successive scans of the swept source laser.

FIG. 3 illustrates a swept source laser with a non-linear tuning through the scan band by plotting the clock frequency as a function of time through successive scans of the swept source laser.

The analog k-clock signal is similar to $\cos(\phi(t))$. When $\phi$ changes by $2\pi$, a clock pulse is issued. The clock frequency is $(1/2\pi)(d\phi/dt)$.

A signal from a mirror would be similar to:

$$\cos((D/2D_{Nyquist})\phi(t)+\phi_0)$$

where D is the mirror displacement. If there is a time delay, T, the clock signal becomes $$\cos(\phi(t+T)) \approx \cos(\phi(t)+T(d\phi/dt))$$

so the clock error, $(T/2\pi)(d\phi/dt)$, is proportional to the clock frequency.

This k-clock frequency error is a problem when the error is not constant as the swept source scans through the scan band—that is, when the sweeps are not linearized. This non-linearity is shown in FIG. 3. Region A corresponds to the k-clock frequency during the scanning of the swept source through the scan band, whereas the region B corresponds to retrace. The frequency of the k-clock is not constant. And thus, the sampling becomes nonlinear when there is a nonzero time delay. This causes broadening of the point-spread functions (PSF) with increasing depth in the sample, because the raw signal becomes chirped. This is not a dispersion-like effect. Dispersion causes a broadening of the PSF independent of depth.

The nonuniform discrete Fourier Transform allows k to vary from an integral value. In this case, x is thought of as a continuous function sampled at a series of $k_n$'s.

$$X[i] = \sum_{n=0}^{N-1} x(k_n) e^{-j\frac{2\pi}{N}ik_n}$$

With nonuniform sampling, the signal, x, is chirped slightly because of the sampling. The NDFT chirps the basis set similarly and the reconstruction is nearly as good as in the nonchirped case. To perform the NDFT, the $k_n$'s need to be measured in a calibration procedure. Once that is done, the basis functions, $\exp(-j(2\pi/N)ik_n)$, is computed. The most straightforward implementation of the calculation is through a simple matrix multiplication, but it is time consuming. Fast nonuniform discrete Fourier transform algorithms exist that can speed up the calculation (L. Greengard, J-Y Lee, Accelerating the Nonuniform Fast Fourier Transform, SIAM Review, vol. 46, no. 3, pp. 443-454).

Experiments have shown that without a k-clock, typical lasers are sufficiently stable to make a reasonable image, but the reconstruction is inferior in its details. When several pairs of interference and clock signals were simultaneously digitized and the point spread functions were computed off line, the paired reconstructions were all similar. However, when non-simultaneous interference/clock signal pairs were reconstructed, i.e., when the k-clock was not delay matched to the optical signals in the interferometer, the point spread functions were noticeably inferior with wider shoulders and sometimes weak sidelobes. These observations argue for a system that incorporates the use of both a concurrent k-clock and nonlinearity compensation using a NDFT algorithm. On the other hand, using an NDFT algorithm with stored clock information would produce inferior results.

Figure 4:
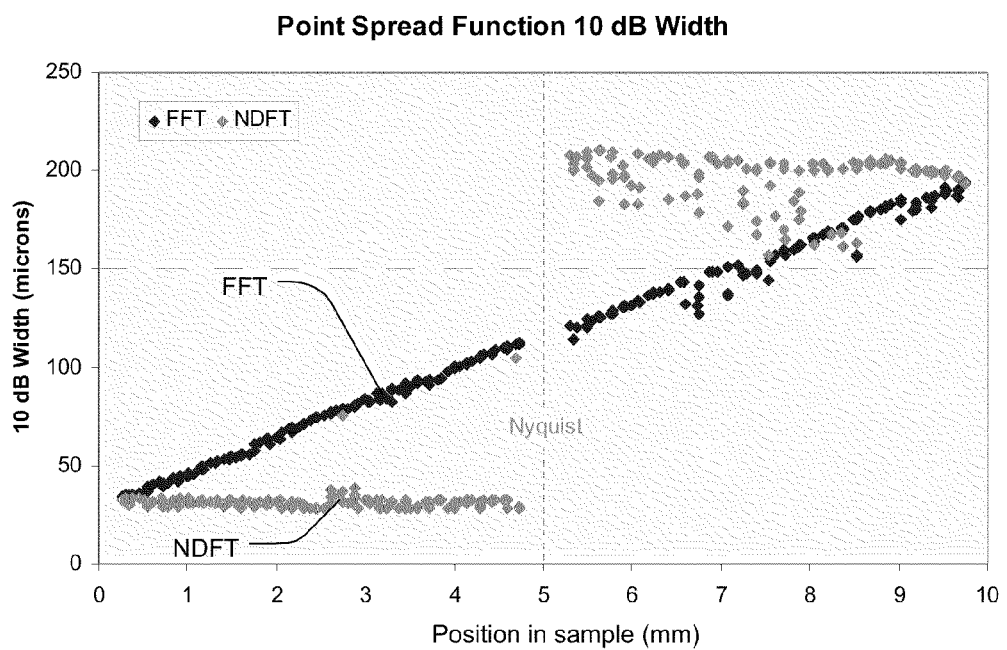
FIG. 4 is a plot of PSF width as a function of position within the sample using a normal discrete Fourier transform (DFT) reconstruction compared with nonuniform discrete Fourier transform (NDFT)

FIG. 4 shows how the PSF width for normal FFT reconstruction increases with depth because of the nonuniform sampling due to the delay mismatch between the k-clock and the optical signals in the interferometer. The width is constant with depth using the NDFT algorithm, at least below the Nyquist point. Beyond that point the compensation effect is of the wrong sign, and there is actually a broadening.

Figure 5:
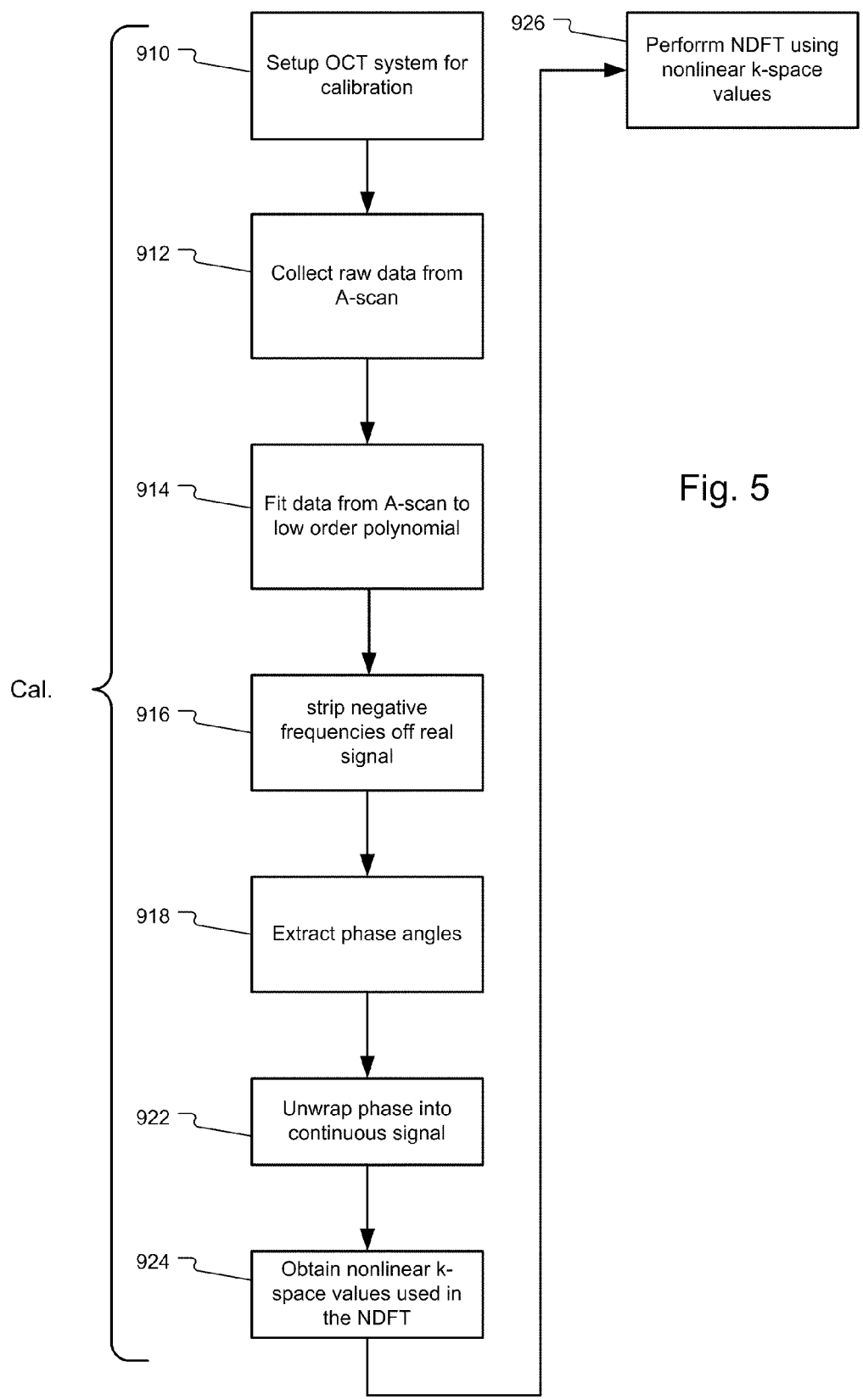
FIG. 5 is a flow diagram showing the calibration and use of the NDFT to obtain the sample images.

FIG. 5 shows the calibration and use of the NDFT to obtain the sample images. Calibration of the system requires calculating or measuring the $k_n$ values. The following procedure is one possible method for doing this:

Set up the OCT system with a simple mirror, instead of a real-world sample in step 910. This method assumes that the main interferometer of the system is dispersion-free. The reflection is preferably positioned somewhere between 0 and the Nyquist distance and the raw data for an A-scan is collected in step 912. The collected data will look like a slightly distorted sine wave.

Then the following computational steps are performed by the processing system 380: (1) Fit the data to a low-order polynomial and subtract it from the raw data in step 914. This makes the Hilbert transform used to remove the negative frequency components from the signal better behaved. (2) Strip the negative frequencies from the signal in step 916. (3) Extract the phase angles from the positive-frequency signal in step 918. (4) Unwrap the phase into a continuous signal, rather than one with $2\pi$ phase jumps in step 922. (5) If the unwrapped phase is $\theta_n$ and the number of points N, then $k_n = (N-1)(\theta_n - \theta_0)/(\theta_{N-1} - \theta_0)$ in step 924. These calculated non-integer k-values characterize the non-linearities in the frequency tuning of the optical signals over the scan band After the k-values are obtained in the calibration, the OCT scans are performed on the sample. The non-linear k-values are then used in the NDFT by the processing system 380 allowing the transformation of the interference signals into an image of a sample in response to the non-linearities.

Figure 6:
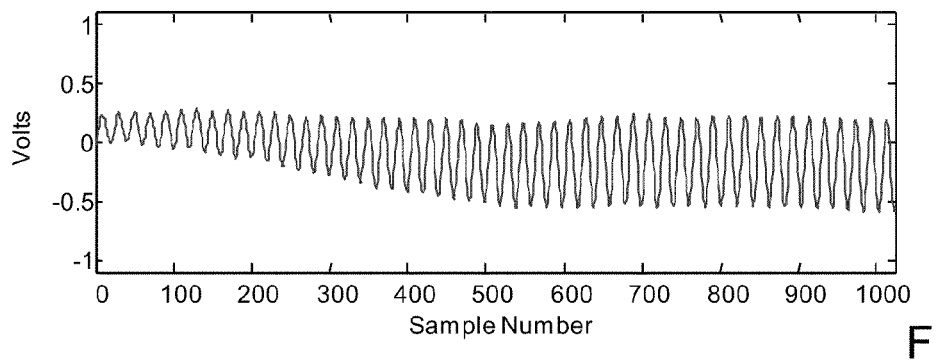
FIG. 6 is a plot of Volts as a function of time showing the interference signal for a feature at 0.5 millimeters (mm)
Figure 7:
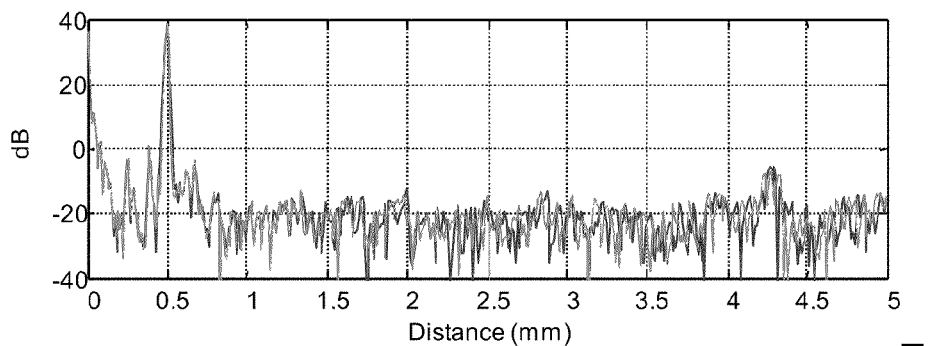
FIG. 7 is a plot of the point spread function at a small depth, 0.5 mm, within the sample when using a standard fast Fourier transform and the NDFT.

FIG. 6 shows the interference signal sampled by the analog to digital converter system 315 for a feature at 0.5 millimeters (mm). FIG. 7 illustrates the point spread function at a small depth within the sample 0.5 mm when using a standard fast Fourier transform and the NDFT. There is negligible difference in performance.

Figure 8:
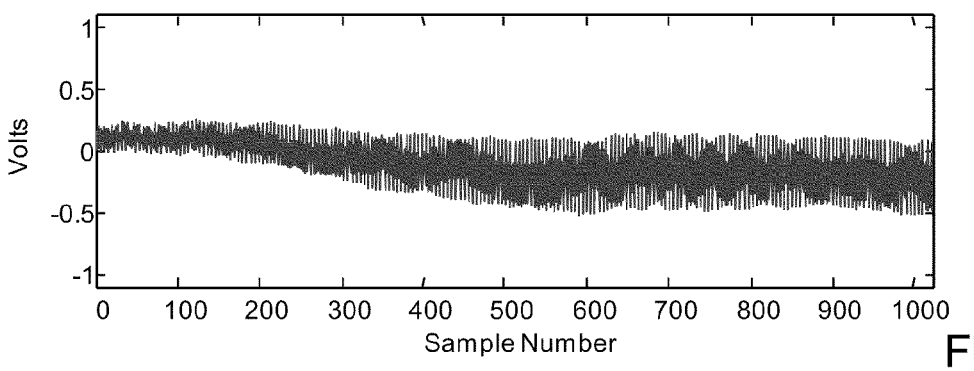
FIG. 8 is a plot of Volts as a function of time showing the interference signal for a feature at 4.0 millimeters (mm)
Figure 9:
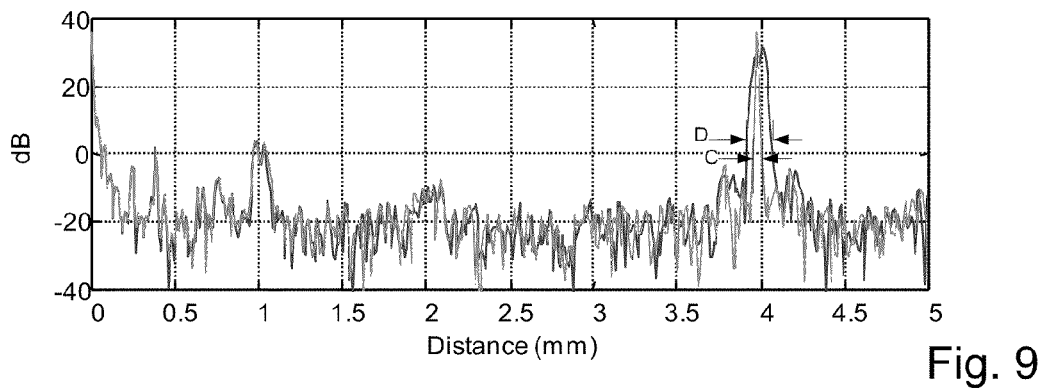
FIG. 9 is a plot of the point spread function at a larger depth, 4.0 mm, within the sample when using a standard fast Fourier transform and the NDFT.

FIG. 8 shows the interference signal sampled by the analog to digital converter system 315 for a feature at 4 mm. FIG. 9 illustrates the point spread function at this 4 mm depth when using a standard fast Fourier transform and the NDFT. Here the PSF for the fast Fourier transform (D) is significantly wider than the PSF for the NDFT (C).

While this invention has been particularly shown and described with references to preferred embodiments thereof, it will be understood by those skilled in the art that various changes in form and details may be made therein without departing from the scope of the invention encompassed by the appended claims.

What is claimed is:

1. An optical coherence analysis system, comprising:
 a swept source laser for generating optical signals that are tuned over a scan band;
 an interferometer for transmitting the optical signals over a sample arm and reference arm and combining the optical signals to generate interference signals;
 a k-clock for generating a sampling clock indicating non-linearities in the frequency tuning of the optical signals over the scan band, the k-clock being not delay matched to propagation delays for the optical signals in the interferometer;
 a sampling system for sampling the interference signals from the interferometer in response to the k-clock; and a processing system for determining non-linearities in the frequency tuning of the optical signals using the k-clock during a calibration and for transforming the interference signals into an image of a sample in response to the non-linearities.

2. A system as claimed in claim 1, wherein a frequency of the k-clock varies as the swept source laser is tuned over the scan band.

3. A system as claimed in claim 1, wherein the processing system performs a nonuniform discrete Fourier transform on the interference signals using non-integer k-values determined in response to the non-linearities.

4. A system as claimed in claim 1, wherein the k-clock is integrated with the swept source laser in a clock laser module.

5. A system as claimed in claim 4, wherein the k-clock signal from the k-clock is conditioned and then directly triggers the sampling system.

6. A system as claimed in claim 1, wherein in the processing system determines the non-linearities by calculating non-integer k-values from a calibration scan in which the sampling system samples the optical signals in response to the k-clock.

7. A system as claimed in claim 6, wherein the sampling system samples the interference signals from the sample in response to the k-clock.

8. An optical coherence analysis method, comprising:
generating optical signals that are tuned over a scan band;
transmitting the optical signals over a sample arm and reference arm of an interferometer and combining the optical signals to generate interference signals;
generating a k-clock indicating non-linearities in the frequency tuning of the optical signals over the scan band that is not delay matched to propagation delays for the optical signals in the interferometer;
sampling the interference signals from the interferometer in response to the k-clock; and
determining non-linearities in the frequency tuning of the optical signals using the k-clock and transforming the interference signals into an image of a sample in response to the non-linearities.

9. A method as claimed in claim 8, wherein a frequency of the k-clock varies as the optical signals are tuned over the scan band.

10. A method as claimed in claim 8, wherein the step of transforming the interference signals comprises performing a nonuniform discrete Fourier transform on the interference signals using non-integer k-values determined in response to the non-linearities.

11. A method as claimed in claim 8, wherein determining the non-linearities comprises calculating non-integer k-values from a calibration scan in which the optical signals are sampled in response to the k-clock.

12. A method as claimed in claim 11, further comprising sampling the interference signals from the sample in response to the k-clock.

13. An optical coherence analysis calibration method, comprising:
generating optical signals that are tuned over a scan band;
transmitting the optical signals over a sample arm and reference arm of an interferometer and combining the optical signals to generate interference signals;
generating a k-clock indicating non-linearities in the frequency tuning of the optical signals over the scan band that is not delay matched to propagation delays for the optical signals in the interferometer;
sampling the interference signals from the interferometer in response to the k-clock;
removing negative frequencies from the interference signals; and
determining non-integer k values that are used in a subsequent nonuniform discrete Fourier transform of the interference signals from a sample.

14. A method as claimed in claim 13, wherein the non-integer k-values are determined from a calibration scan in which the optical signals are sampled in response to the k-clock.

15. A method as claimed in claim 14, further comprising sampling the interference signals from the sample in response to the k-clock.

16. An optical coherence analysis system, comprising:
a swept source for generating optical signals that are tuned over a scan band;
an interferometer for transmitting the optical signals over a sample arm and reference arm and combining the optical signals to generate interference signals;
a k-clock for generating a sampling clock indicating non-linearities in the frequency tuning of the optical signals over the scan band, the k-clock being not delay matched to propagation delays for the optical signals in the interferometer;
a sampling system for sampling the interference signals from the interferometer in response to the k-clock; and
a processing system for determining non-linearities in the frequency tuning of the optical signals using the k-clock during a calibration and for transforming the interference signals into an image of a sample in response to the non-linearities.

17. A system as claimed in claim 16, wherein a frequency of the k-clock varies as the swept source is tuned over the scan band.

18. A system as claimed in claim 16, wherein the processing system performs a nonuniform discrete Fourier transform on the interference signals using non-integer k-values determined in response to the non-linearities.

19. A system as claimed in claim 16, wherein the k-clock is integrated with the swept source in a clock module.

20. A system as claimed in claim 19, wherein the k-clock signal from the k-clock is conditioned and then directly triggers the sampling system.

21. A system as claimed in claim 16, wherein in the processing system determines the non-linearities by calculating non-integer k-values from a calibration scan in which the sampling system samples the interference signals in response to the k-clock.

22. A system as claimed in claim 21, wherein the sampling system samples the interference signals from the sample in response to the k-clock.

* * * * *